(12) United States Patent
Anderson et al.

(10) Patent No.: US 8,128,606 B2
(45) Date of Patent: Mar. 6, 2012

(54) OPHTHALMIC APPARATUS AND METHOD FOR ADMINISTERING AGENTS TO THE EYE

(75) Inventors: Daryl E. Anderson, Corvallis, OR (US); John Stephen Dunfield, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1915 days.

(21) Appl. No.: 10/613,842

(22) Filed: Jul. 3, 2003

(65) Prior Publication Data

US 2005/0001981 A1    Jan. 6, 2005

(51) Int. Cl.
*A61M 35/00* (2006.01)
*A61M 31/00* (2006.01)
*A61B 13/00* (2006.01)

(52) U.S. Cl. .......... 604/300; 604/294; 604/295; 604/65; 600/558

(58) Field of Classification Search ............ 604/65, 604/66, 67, 289, 294–302, 521; 600/558, 600/236; 351/205, 231

See application file for complete search history.

(56) References Cited

U.S. PATENT DOCUMENTS

| | | | | |
|---|---|---|---|---|
| 3,756,073 A | * | 9/1973 | Lavallee et al. | 600/401 |
| 4,145,122 A | * | 3/1979 | Rinard et al. | 351/210 |
| 4,573,982 A | * | 3/1986 | Forbes et al. | 604/300 |
| 4,659,197 A | * | 4/1987 | Weinblatt | 351/210 |
| 4,683,481 A | | 7/1987 | Johnson | |
| 4,838,681 A | * | 6/1989 | Pavlidis | 351/210 |
| 4,992,808 A | | 2/1991 | Bartky et al. | |
| 5,002,384 A | | 3/1991 | Trachtman | |
| 5,107,851 A | * | 4/1992 | Yano et al. | 600/405 |
| 5,171,306 A | * | 12/1992 | Vo | 604/295 |
| 5,278,584 A | | 1/1994 | Keefe et al. | |
| 5,368,582 A | | 11/1994 | Bertera | |
| 5,373,964 A | * | 12/1994 | Moore | 222/1 |
| 5,420,627 A | | 5/1995 | Keefe et al. | |
| 5,523,808 A | * | 6/1996 | Kohayakawa | 351/210 |
| 5,555,895 A | * | 9/1996 | Ulmer et al. | 600/558 |
| 5,627,611 A | * | 5/1997 | Scheiner | 351/158 |
| 5,634,463 A | * | 6/1997 | Hayafuji | 600/405 |
| 5,692,492 A | * | 12/1997 | Bruna et al. | 128/200.23 |
| 5,807,357 A | | 9/1998 | Kang | |
| 5,830,139 A | * | 11/1998 | Abreu | 600/405 |
| 5,836,927 A | * | 11/1998 | Fried | 604/300 |
| 5,928,662 A | | 7/1999 | Phillips | |
| 5,988,815 A | | 11/1999 | Maus et al. | |
| 6,030,343 A | * | 2/2000 | Chechersky et al. | 600/399 |
| 6,053,867 A | * | 4/2000 | Iijima | 600/399 |
| 6,149,968 A | | 11/2000 | Shimada | |
| 6,159,186 A | * | 12/2000 | Wickham et al. | 604/251 |
| 6,186,619 B1 | | 2/2001 | Usui et al. | |
| 6,193,343 B1 | | 2/2001 | Norigoe et al. | |
| 6,270,467 B1 | | 8/2001 | Yee | |
| 6,280,436 B1 | | 8/2001 | Freeman et al. | |

(Continued)

FOREIGN PATENT DOCUMENTS

JP    2004041465 A   *   2/2004

(Continued)

*Primary Examiner* — Leslie Deak
*Assistant Examiner* — Susan Su

(57) ABSTRACT

Embodiments of an ophthalmic apparatus are disclosed for administering fluids to the eye. In one disclosed embodiment, the ophthalmic apparatus includes an eye-positioning device for assisting a subject in positioning an eye in a desired position for administering the fluid and a fluid applicator for dispensing the fluid into the eye when the eye is in the desired position.

34 Claims, 5 Drawing Sheets

U.S. PATENT DOCUMENTS

| | | | |
|---|---|---|---|
| 6,299,305 B1 * | 10/2001 | Miwa | 351/200 |
| 6,409,343 B1 * | 6/2002 | Uchida | 351/208 |
| 6,467,905 B1 * | 10/2002 | Stahl et al. | 351/202 |
| 6,494,577 B2 | 12/2002 | Iwanaga | |
| 6,520,640 B1 | 2/2003 | Binnun | |
| 6,542,081 B2 * | 4/2003 | Torch | 340/575 |
| 6,569,131 B1 * | 5/2003 | Michael et al. | 604/295 |
| 6,595,920 B2 * | 7/2003 | Walton | 600/401 |
| 6,832,200 B2 * | 12/2004 | Greeven et al. | 705/3 |
| 6,945,650 B2 * | 9/2005 | Beverly | 351/208 |
| 7,153,266 B2 * | 12/2006 | Uchida | 600/399 |
| 7,496,174 B2 * | 2/2009 | Gertner et al. | 378/65 |
| 2002/0013573 A1 * | 1/2002 | Telfair et al. | 606/5 |
| 2002/0096186 A1 * | 7/2002 | Von Halem | 132/333 |
| 2003/0135169 A1 * | 7/2003 | Cohen et al. | 604/295 |
| 2004/0204674 A1 * | 10/2004 | Anderson et al. | 604/66 |
| 2004/0267214 A1 * | 12/2004 | Kerssies | 604/299 |

FOREIGN PATENT DOCUMENTS

WO     WO 00/16961     3/2000

* cited by examiner

OPHTHALMIC APPARATUS AND METHOD FOR ADMINISTERING AGENTS TO THE EYE

FIELD

This invention relates to embodiments of a device and method for administering fluids to the eye.

BACKGROUND

Many people suffer from Keratitis Sicca (common dry eye), resulting in discomfort and possible ocular damage from desiccation of the cornea. A less common medical condition that prevents the eyelid from naturally wetting the eye is Bell's palsy. Bell's palsy is a condition that causes unilateral facial paralysis that interferes with the ability to blink or close the eye. Dry eye conditions are typically treated with artificial tear solutions to restore the corneal tear film layer and relieve discomfort. However, the application of an artificial solution often provides only temporary relief and therefore must be applied many times throughout the day. The burden caused by frequent application of eye drops can be a disincentive to applying the drops to maintain proper corneal tear film moisture levels.

Another ophthalmic condition, Nocturnal Lagophthalmos, causes the eyelid to remain partially open during sleep, which allows desiccation of the exposed portion of the cornea. A common treatment for this condition involves instilling a viscous ointment (a lubricant) in the eye before going to sleep. Although effective to avoid nocturnal corneal desiccation, use of the ointment can be messy, which is often a disincentive to its use.

Many ophthalmic medical conditions can be effectively treated by periodic instillation of pharmaceutical agents into the eye. Beta blockers for the treatments of glaucoma and antibiotics for the treatment of corneal infections are examples of such agents. However, effective treatment often requires periodic and regular administration of the drug to achieve the desired therapeutic effect.

Devices and methods are disclosed herein for improving the introduction or instillation of fluids into the eye, for example by applying wetting solutions to the eye or for administering therapeutic agents that treat ocular conditions.

SUMMARY

The present disclosure concerns embodiments of an ophthalmic apparatus and methods for its use. In one embodiment, the ophthalmic apparatus includes an eye-positioning device for assisting a subject in positioning an eye in a desired position for administering a fluid. A fluid applicator dispenses the fluid into the eye when the eye is in the desired position.

DETAILED DESCRIPTION

Figure 1:
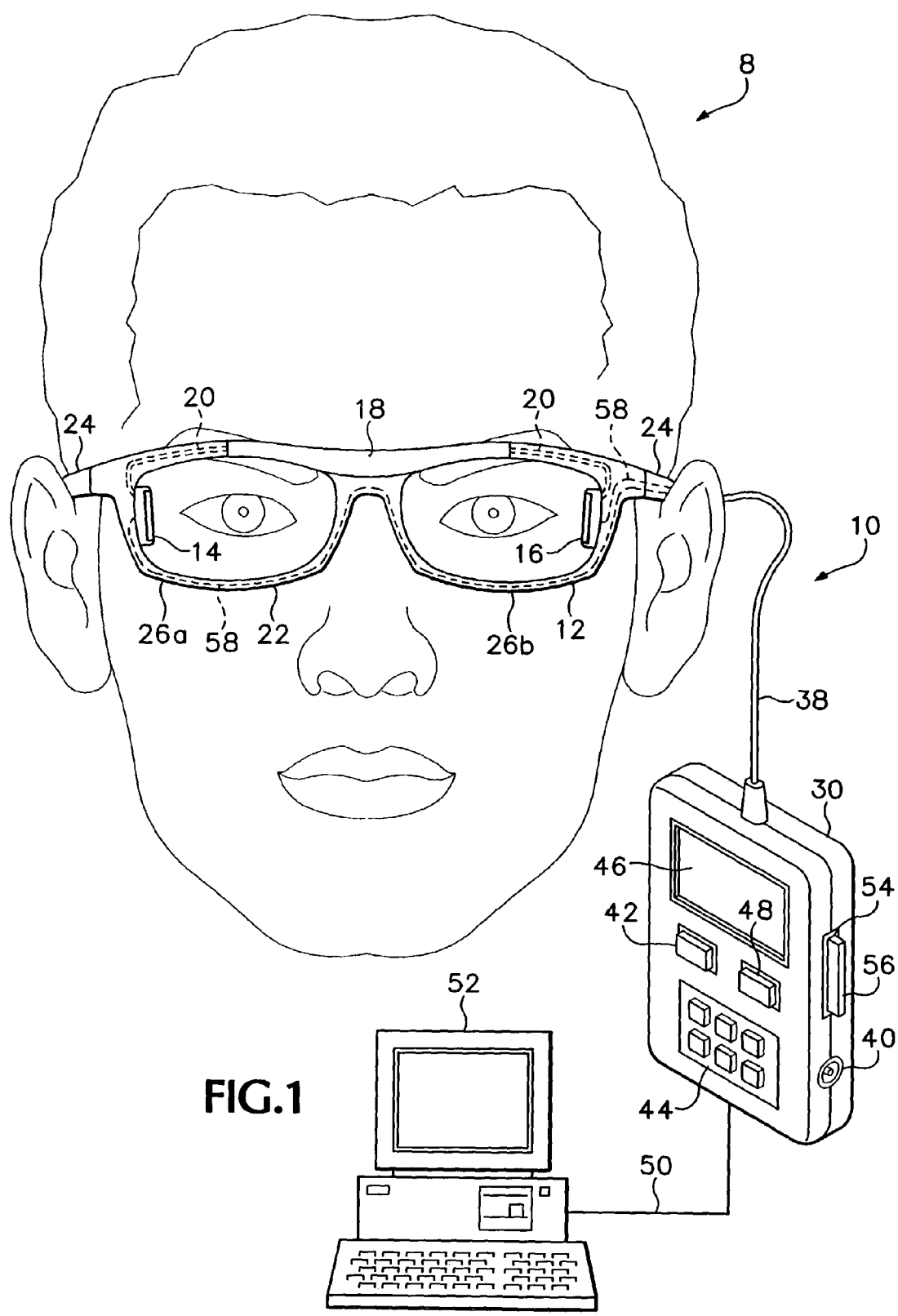
FIG. 1 is a perspective view of one embodiment of the ophthalmic apparatus for administering a fluid into one or both eyes of a subject.

Unless otherwise noted, technical terms are used according to conventional usage. Definitions of common terms in pharmacology may be found in *Remington: The Science and Practice of Pharmacy*, 19$^{th}$ Edition, published by Mack Publishing Company, 1995 (ISBN 0-912734-04-3).

The singular forms "a," "an," and "the" refer to one or more than one, unless the context clearly dictates otherwise.

As used herein, the term "comprises" means "includes."

As used herein, a group of individual members stated in the alternative includes embodiments relating to a single member of the group or combinations of multiple members. For example, the term "antibiotic, bronchodilator, or vitamin," includes embodiments relating to "antibiotic," "bronchodilator," "vitamin," "antibiotic and bronchodilator," "bronchodilator and vitamin," "antibiotic and vitamin," and "antibiotic, bronchodilator, and vitamin."

A "bioactive" composition, substance, or agent is a composition that affects a biological function of a subject to which it is administered. An example of a bioactive composition is a pharmaceutical substance, such as a drug or antibiotic, which is given to a subject to alter a physiological condition of the subject, such as a disease. Bioactive substances, compositions, and agents also include other biomolecules, such as proteins and nucleic acids, or liposomes and other carrier vehicles that contain bioactive substances. Bioactive compositions also may include pharmaceutical carriers, adjuvants, and salts.

"Drug" includes any bioactive composition administered for a therapeutic (including diagnostic) purpose.

As used herein, the term "jet dispenser" refers to a fluid dispenser having a construction similar to an inkjet dispenser used in inkjet printing technology. The construction of the jet dispensers in the disclosed embodiments can be modified from a conventional inkjet construction to accommodate, for example, the characteristics of the particular fluid to be dispensed. In the embodiments disclosed herein, the jet dispensers can be, for example, a piezoelectric inkjet type dispenser or a thermal inkjet type dispenser, both of which are further discussed below.

The present disclosure concerns embodiments of an ophthalmic apparatus and methods for its use. In particular embodiments, the ophthalmic apparatus includes an eye-positioning device for assisting the subject in positioning an eye in a desired position for administering a fluid to the eye and an applicator for dispensing the fluid into the eye when the eye is in the desired position. The applicator in one embodiment includes a frame for wearing on the head of a user and a fluid dispenser supported by the frame. The fluid dispenser receives fluid from a fluid reservoir, which also may be supported by the frame, and dispenses a controlled amount of the fluid into the eye. In some embodiments, two fluid dispensers are mounted to or otherwise supported by the frame, with each fluid dispenser positioned to dispense fluid into an adjacent eye. In an illustrated embodiment, the frame is a conventional spectacle frame. The frame can support lenses and therefore can also serve as a pair of eyeglasses.

The apparatus can be used to introduce various fluids into one or both eyes of a user. For example, the apparatus can be used to dispense an artificial tear solution into one or both eyes to maintain proper moisture levels. Alternatively, the apparatus can be used to dispense a bioactive composition in a liquid carrier into one or both eyes for treating various ocular conditions.

In particular embodiments, the fluid dispenser is a jet dispenser, such as a thermal jet dispenser or a piezoelectric jet dispenser, having a construction similar to an inkjet dispenser used in inkjet printing technology. The jet dispenser is operable to propel precise amounts of fluid in the form of small droplets into the eye.

In some embodiments, the eye-positioning device includes an eye-position detector for detecting the position of the eye relative to the desired position. The eye-position detector can include an image pick-up device, such as a conventional digital camera, for capturing an image of the eye, and an image processor. The image processor receives the image from the image pick-up device and determines whether the eye is in the desired position for administering the fluid to the eye.

The apparatus also may include a feedback mechanism for providing feedback information to assist the user in moving the eye to the desired position for administering the fluid. In particular embodiments, the feedback mechanism provides feedback information in the form of feedback signals or cues (e.g., audible or visual signals) that correspond to directions for moving the eye to the desired position. For example, the feedback signals can be vocalizations, such as, "move eye to right," "move eye to left," "move eye down," "move eye up," or similar instructions.

The apparatus also may include a controller for manually or automatically dispensing the fluid from the dispenser at selected times and at specified rates. The controller may take the form of an actuator that is manually depressed to activate the dispenser and dispense the fluid. Alternatively, the controller may be a programmable device, such as a microprocessor, that is programmed to dispense the fluid at predetermined intervals, for example several times a day. In some embodiments, the controller includes an audible or visible cue, such as a tone or light, to alert the subject that a dose of the fluid is ready to be dispensed. Alternatively, the controller may be used to adjust the dosage of an administered drug for a particular circumstance, such as a particular time of day, an event (such as an activity that will require a dosage modification), or detection of a physiological condition (such as an adverse drug reaction that requires reduction or cessation of drug administration). Complex administration protocols may be followed, for example applying different drugs at different times throughout the day or for longer periods, such as a week, a month, or even longer.

In particular embodiments, a user interface software program is used to acquire user input for setting various operating parameters of the apparatus, such as dosage amounts and dispensing rates. Also, a user can select, via the program, the specific location on the eye surface on which the fluid is to be dispensed, such as the corner or center of the eye. The program then determines the proper position for the eye that will allow the fluid dispenser to dispense fluid onto the selected location on the eye surface. In one embodiment of the user interface program, a user can input various operating parameters of the apparatus via graphical user interface elements.

Using existing inkjet technology, exact dosing of a fluid into an eye may be achieved. In addition, controllers may be used to dispense simple or complex drug regimens. Computerized control of medication dosing, which may be programmed by medical personnel for subsequent automated delivery, can help avoid toxic drug interactions, overdoses, and deaths.

The dispensers disclosed herein may be similar to fluid dispensers known as inkjet printheads used in inkjet printing mechanisms, such as printers, plotters, facsimile machines and the like, some of which are described, for example, in Durbeck and Sherr, *Output Hardcopy Devices*, Academic Press Inc., 1987 (ISBN 0-12-225040-0), particularly in chapter 13, pages 311-370. These technologies have in common the extraction of a small quantity of a fluid from a reservoir that is converted into fine droplets and transported through the air to a target medium by appropriate application of physical forces. This technology has been implemented in a variety of ways, but one of the common approaches has been thermal inkjet technology, in which liquids are heated using resistors to form drops and propel them from a chamber through an orifice toward a target. Another approach is piezoelectric inkjet technology, in which movement of a piezoelectric transducer changes a chamber volume to generate the drop.

A typical jet printing mechanism uses cartridges (often called "pens") which shoot drops of liquid colorant (generally referred to as "ink") onto a page. Each cartridge includes a printhead formed with very small nozzles through which the ink drops are fired. Most often, the printhead is held in a carriage which slides back and forth along a guide rod in a reciprocating printhead system, with a target or print media, such as paper, being advanced in steps between each pass of the printhead. To print an image on media, the printhead is scanned back and forth across the page, shooting drops of ink in a desired pattern as it moves. Other printing systems known as "page-wide array" printers, extend the printhead across the entire page in a stationary location and print as the media advances under the printhead. The particular liquid ejection mechanism within either type of printhead may take on a variety of different forms, such as the piezoelectric or thermal printhead technology.

For example, two thermal ink ejection mechanisms are shown in U.S. Pat. Nos. 5,278,584 and 4,683,481, both assigned to the Hewlett-Packard Company. In a thermal system, a barrier layer containing fluid channels and vaporization chambers is located between a nozzle orifice plate and a substrate layer. The substrate layer typically contains linear arrays of heater elements, such as resistors, which are energized to heat ink within the vaporization chambers. Upon heating, an ink droplet is ejected from a nozzle associated with the energized resistor. By selectively energizing the resistors as the printhead moves across the page, the ink is expelled in a pattern on the print media to form a desired image (e.g., picture, chart, or text).

In piezoelectric inkjet technology, an activating pulse is applied to a piezoelectric plate or member attached to a plate, which then responds by flexing to propel an ink drop out of a nozzle. Several examples of piezo-electric ink-jet printheads are described in U.S. Pat. Nos. 4,992,808; 6,186,619; and 6,149,968 and 6,193,343 and WO 00/16981.

In a common cartridge configuration, both the fluid reservoir and the printhead are carried by a carriage along the guide rod of the printer. Such printers are known as an "on-axis" printers. Some on-axis printers use "snapper" reservoir systems, in which permanent or semi-permanent printheads are used in conjunction with a detachable reservoir carrying a fresh liquid supply, with the reservoir being snapped into place on the printhead. Another design uses permanent or semi-permanent printheads in what is known in the industry as an "off-axis" printer. In an off-axis system, the printheads carry only a small liquid supply reciprocally back and forth across the printzone, with this on-board supply being replenished through tubing that delivers liquid from an "off-axis main reservoir" placed at a remote, stationary location within or near the printhead. In both the snapper and off-axis systems, rather than purchasing an entire new cartridge which includes a costly new printhead, the consumer buys only a new supply of liquid for the main reservoir or a replacement reservoir already filled with fluid.

In striving to duplicate the quality of photographic film images, the ink-jet industry has focused on decreasing the size of ink droplets ejected from the nozzles, as well as accurately placing these droplets on the print media. For instance, some of the more recent inkjet print cartridges are able to deliver droplets about 3-6 picoliters in volume, although larger droplets also may be generated, for example droplets of 10, 50, 100, or more picoliters. The resolution within which currently commercially available inkjet printing mechanisms may place ink droplets on a page is on the order of 1200-2400 dots per inch (known in the industry as a "dpi" rating). Thus, while striving to achieve photographic print quality, inkjet printing technology has become very adept at accurately metering and dispensing fluids. This ability to dispense very small and accurate amounts of fluids (including liquids and powders) is a part of the application systems illustrated herein.

In particular embodiments, the droplet sizes are about 20 pL to 40 pL, although in other embodiments the droplet sizes can be smaller than 20 pL or larger than 40 pL. The size of the droplets ejected from a jet dispenser depends in part on the size of the orifice through which the droplets are ejected. In this regard, some printheads include multiple orifices of varying sizes. This allows a single printhead to be used to selectively dispense droplets of different sizes.

In another representative embodiment, an ophthalmic apparatus includes an eye-position detector for detecting the current position of an eye of a subject and a feedback device for providing feedback information that assists the subject in moving the eye from the current position to a predetermined position for administering a fluid to the eye. The apparatus also may include a dispensing apparatus for automatically dispensing a fluid into the eye when the eye-position detector detects that the eye is in the predetermined position.

In still another representative embodiment, an ophthalmic apparatus for administering a liquid to an eye of a subject includes detecting means for detecting the position of the eye and dispensing means for dispensing the liquid into the eye when the eye is in a predetermined position. In particular embodiments, the detecting means includes means for capturing an image of the eye and processing means for detecting the position of the eye relative to the predetermined position based on the image of the eye. The apparatus may further include feedback means for providing feedback to the subject to assist the subject in moving the eye to the predetermined position if the detecting means detects that the eye is not in the predetermined position.

In yet another representative embodiment, a method for administering a liquid to an eye of a subject includes detecting the position of the eye relative to a predetermined position with an eye-position detector and dispensing the liquid into the eye with a liquid dispenser if the eye is in the predetermined position. If the eye is not in the predetermined position, feedback information can be provided to the subject so that the subject can move the eye to the predetermined position.

More specifically, and referring to FIG. 1, there is shown one embodiment of a dispensing apparatus (also referred to herein as an applicator), indicated generally at 10, for administering a fluid to one or both eyes of a user 8. The apparatus 10 in the illustrated configuration includes a spectacle-like frame 12 that is worn on the head of the user like conventional spectacles. Mounted to the frame 12 are fluid dispensers 14 and 16 positioned to dispense fluid into the eyes of the user 8. The illustrated apparatus 10 also includes a fluid reservoir 18 for containing the fluid to be administered to the eyes of the user. The illustrated fluid reservoir 18 is mounted to the frame 12 and is fluidly connected to the dispensers 14,16 via fluid conduits 20. The frame 12 also can serve as a mount for optical or protective lenses and therefore function as a pair of eyeglasses, sunglasses, or other protective eyewear.

Although the illustrated frame 12 resembles conventional spectacles, this is not a requirement. Hence, the frame can be any structure generally configured to support the fluid dispensers 14,16 at a convenient position for dispensing fluid into the eyes. For example, the brim of a hat can serve as a frame for supporting the dispensers 14,16

The illustrated fluid dispensers 14,16 are inkjet-type jet dispensers, such as thermal droplet jet dispensers or piezoelectric droplet jet dispensers, having multiple ejection orifices, or nozzles, (not shown) that dispense small droplets of fluid. For example, the dispensers 14,16 can have about 300 orifices per inch, although dispensers with greater or fewer number of orifices also can be used. The construction of dispensers 14, 16 is conventional, such as disclosed in U.S. Pat. No. 5,420,627 to Keefe et al., U.S. Pat. No. 5,278,584 to Keefe et al., U.S. Pat. No. 4,683,481 to Johnson, U.S. Pat. No. 4,992,808 to Bartky et al., U.S. Pat. No. 6,186,619 to Usui et al., U.S. Pat. No. 6,149,968 to Shimada and U.S. Pat. No. 6,193,343 to Norigoe et al. In alternative embodiments, fluid dispensers other than jet dispensers can be used for dispensing fluid from the fluid reservoir 18, although jet dispensers are preferred due to their excellent accuracy and repeatability. For example, the apparatus can include one or more miniature fluid pumps (e.g., a miniature positive-displacement pump) not having a conventional inkjet-type construction.

The illustrated frame 12 has an eye-piece 22 that rests on the bridge of a user's nose and two arms 24 that extends behind the user's ears. The dispensers 14, 16 are shown mounted to the outside portions of rims 26a, 26b, respectively, of the eye-piece 22 adjacent the arms 24. However, dispensers 14, 16 can be mounted at other convenient positions on the frame 12. For example, the dispensers can be mounted to the inside portions of rims 26a, 26b of the eye-piece 22 adjacent the user's nose or to the portions of rims 26a, 26b above or below the eyes.

Figure 3:
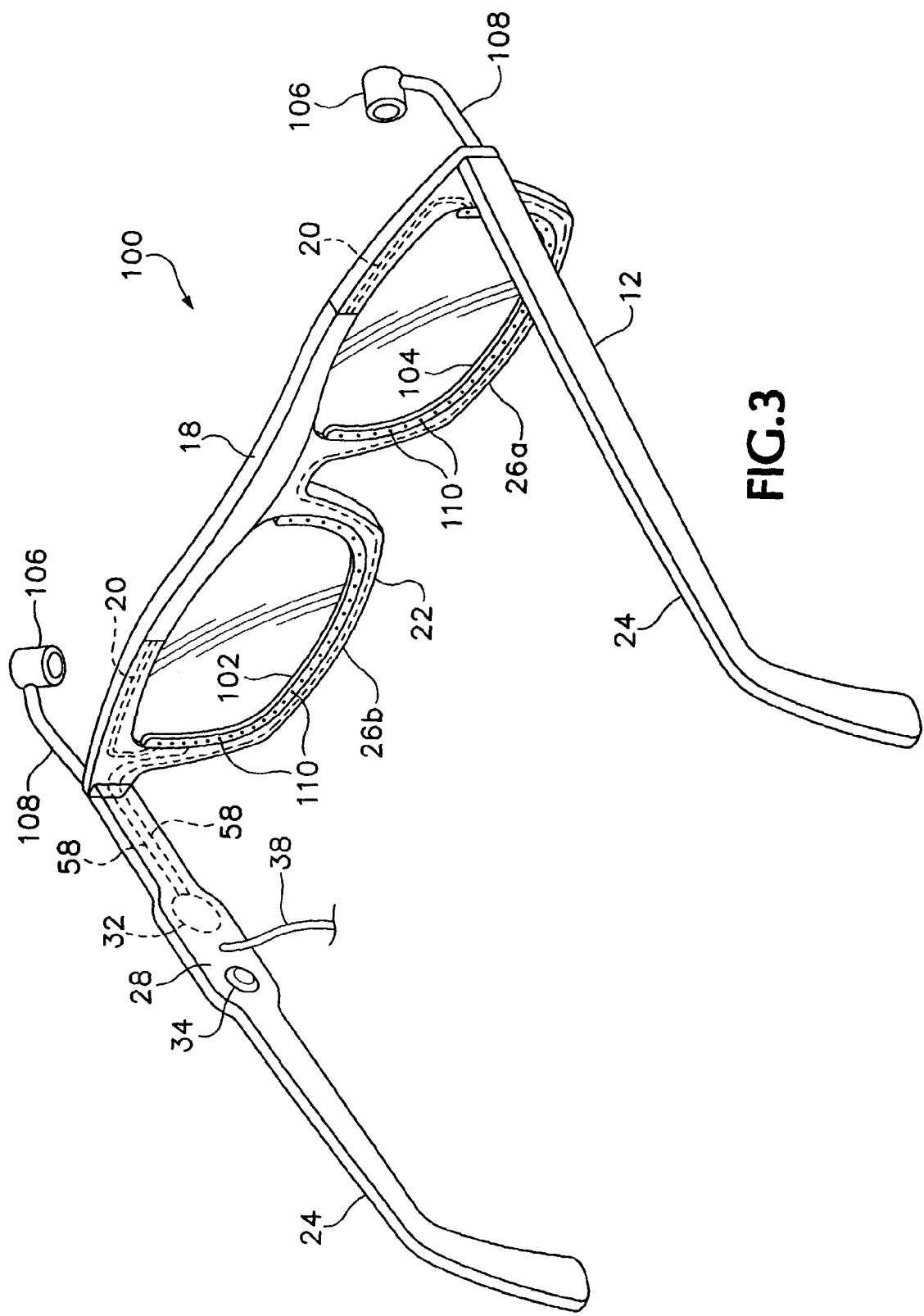
FIG. 3 is a perspective view of another embodiment of the ophthalmic apparatus.

While the illustrated embodiment is shown as having two fluid dispensers 14, 16 mounted to the eye-piece 22 of the frame 12, other embodiments may include only one such dispenser mounted to the eye-piece 22 or more than two dispensers mounted at other positions on the eye-piece 22. In addition, the illustrated dispensers 14, 16 are rectangular in shape, though dispensers of different shapes also can be used. For example, each dispenser 14, 16 can be configured to generally conform to the shape of the rims 26a, 26b of the eye-piece 22 (as shown in FIG. 3).

The fluid reservoir 18 desirably is a removable and replaceable cartridge. In this configuration, a user can replace the currently installed cartridge with another cartridge filled with the selected fluid. Thus, when a cartridge is emptied of fluid, it is simply removed and replaced. In addition, this configuration allows a user to easily change cartridges for dispensing a different type of fluid.

In addition, in other embodiments, multiple fluid reservoirs can be removably or permanently mounted to the frame for containing different types of fluid. In still other embodiments, one or more fluid reservoirs are fluidly connected to the dispensers 14, 16 via fluid conduits, but are otherwise not mounted to or supported by the frame 12. For example, a fluid reservoir can be carried by the user 8, such as in a shirt pocket. In the latter configuration, the fluid reservoir may include a pump for pumping the stored fluid from the fluid reservoir to the dispensers 14,16.

Figure 2:
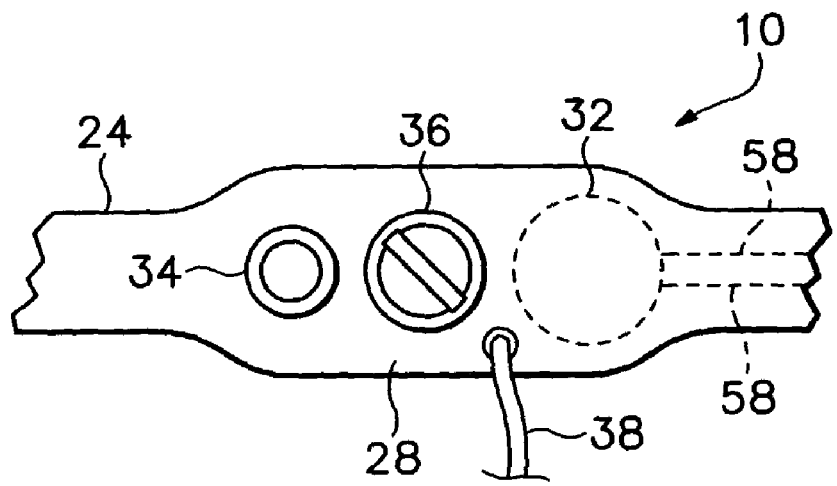
FIG. 2 is a side view of a portion of the frame of the apparatus of FIG. 1.

The apparatus can apply, among other fluids, lubricating or medicating liquid to the topical surface of a user's eye. The fluid reservoir 18 holds a supply of fluid and delivers the fluid to the dispensers 14,16 via the fluid conduits 20. The illustrated apparatus 10 includes a first controller 28 (as shown in FIG. 2) housed within an arm 24 of the frame 12, and also may include a second, hand-held controller 30 (as shown in FIG. 1) for controlling the operation of the dispensers 14, 16. Controller 28 includes a battery 32 electrically connected to dispensers 14,16 via wires 58 to power the dispensers 14,16. An ON/OFF button 34 of controller 28 enables a user to turn the dispensers 14,16 on and off. The controller 28 can include an additional ON/OFF button (not shown), with each ON/OFF button controlling one of the dispensers 14, 16, to allow a user to selectively activate either one or both of the dispensers. The illustrated controller 28 also includes a rate adjuster 36 for controlling the dispensing rates of the dispensers 14,16. By rotating the rate adjuster 36, either clockwise or counter clockwise, a user can selectively increase or decrease the rate at which droplets are dispensed from the orifices of the dispensers 14, 16.

Controller 28 also may include a programmable memory that can be programmed, for example, by controller 30 to control additional operating parameters of the dispenser 14, 16. The operating parameters can be, without limitation, variations in the amount of and types of fluids dispensed, the rate at which a fluid is dispensed from each dispenser 14, 16, the duration between fluid ejection sequences, and the times of day that the apparatus is to begin and stop dispensing fluid. For example, for a person with chronic dry eye condition, the controller 28 can be programmed to dispense a small amount of lubricant into one or both eyes every few hours (e.g., about every 2-3 hours or as needed to maintain proper moisture levels in the eyes). As another example, if the user suffers from lack of eye moisture during sleep because of a sleep disorder (e.g., Nocturnal Lagophthalmos), the controller 28 can be programmed to automatically begin dispensing fluid at a time when the user expects to be asleep, and then automatically stop dispensing fluid at the usual wake-up time of the user.

The controller 28 also can be programmed to activate specific nozzles or a range of nozzles of the dispensers 14, 16 when applying fluid into the eyes. For example, when using the apparatus to lubricate the eyes during waking hours, it may be desirable to activate all or nearly all of the nozzles of dispensers 14, 16 to maximize coverage over the surface area of the eyes. As another example, a patient that suffers from Nocturnal Lagophthalmos could program the controller 28 to dispense fluid from selected nozzles that are positioned to dispense droplets into the partially opened eye so as to prevent fluid from being sprayed onto the eyelid.

The controller 28 also may be programmed to prevent unauthorized alteration of dosages, for example an increase in a dosage of a controlled substance above that authorized by the prescribing physician. Alternatively, the controller can permit certain ranges of dosages to be administered.

As shown in FIG. 1, the controller 30 is electrically connected to controller 28 on the frame 12 via a connector 38. Other linkage devices may be used to communicate between controller 28 and controller 30, such as by using infrared signals, radio waves, and the like. Controller 30 can be used to set the operating parameters that are sent to the programmable memory of controller 28. In this manner, controller 30 serves as an input device for controller 28. Controller 30 also can be used to directly control the operation of dispensers 14, 16. In the latter example, controller 28 would serve merely an electrical interface between controller 30 and the dispensers 14, 16 and therefore would not require a memory device.

The controller 30 can be configured to receive power either from an onboard battery storage system, or alternatively, power may be supplied from an external source, such a standard electrical outlet. Of course, rechargeable or replaceable batteries may be preferred in some embodiments for ease of portability and use. In particular embodiments, the controller 30 houses one or more rechargeable batteries and includes an input power slot 40, which accepts a standard AC/DC adapter (not shown) to power the controller and/or recharge the batteries. Battery 32 also can be a rechargeable batter that is automatically recharged when controller 30 is electrically connected to controller 28 and the controller 30 is connected to an electrical outlet with the AC/DC adapter.

In a simple embodiment, controller 30 may include an ON/OFF power switch, or button, 42, to which controller 30 responds by beginning and/or ending a fluid ejection sequence. Alternatively, switch 42 may simply serve as an ON switch, with controller 30 determining the precise amount of fluid to be ejected from the fluid dispensers, and then stopping ejection automatically after the selected metered amount has been dispensed.

In a more sophisticated embodiment, controller 30 may include one or more input devices, such as an input keypad 44, which can be an alpha or alpha numeric keypad. Using keypad 44, a physician, nurse, pharmacist or other health professional, or the subject to which the fluid will be administered, may input various operating parameters, such as the operating parameters discussed above. Controller also may include a display screen 46, which can be a liquid crystal display, to indicate which selections have been made using keypad 44 and/or to display different operating parameters of the apparatus 10. Alternatively, keypad 44 may be eliminated, and the controller 30 programmed to display various selections on screen 46. Buttons 42 and 48 may serve as scrolling buttons to allow different instructions or selections to be scrolled across, or up and down along, screen 46, including information such as desired dosages, frequency, and potential side effects.

In still other alternative embodiments, the display screen 46 also is a touch screen, in addition to, or in place of, keypad 44. The touch screen may include a series of images that, when touched with a finger or stylus, program the controller 30. Alternatively, the touch screen may include a character recognition area for receiving written inputs using a stylus, such as the graffiti recognition features of the Palm® operating system (Palm, Inc., Santa Clara, Calif.). Thus, a touch screen provides an alternative means for programming the controller in addition to the keypad.

As shown in FIG. 1, a more expedient method of initially programming controller 30 and/or controller 28, or supplying dosage and other information, may be to use a computer input link 50, selectively attachable to the controller 30, to couple an external computer, microcomputer, or other computing device 52 to controller 30. Other linkage devices may be used to communicate between external computing device 52 and controller 30, such as by using infrared signals, radio waves, modems, direct connections, and the like. In another implementation, the computing device 52 can communicate directly with controller 28 through a suitable linkage device, in which case controller 30 would not be used.

For example, a patient can download information stored in either controller 28 or controller 30 about self-regulated dosage administrations or symptoms experienced (as indicated for example by which buttons have been depressed on the device, and/or the pattern and frequency of the buttons that are pushed). This information can be transmitted over a modem to a physician's or other health care provider's office, where it can be displayed (in electronic or other form) to a health care professional, and appropriate action can be taken. For example, if symptoms are noted to be increasing in spite of administration of a therapeutic amount of a particular drug, consideration can be given to providing a new drug or reconsidering the diagnosis for which the drug has been administered. As another example, the controller 30 may include a docking connection for use with a docking station connected to a computer at the physician's office. Thus, connecting the apparatus to an external computer provides an alternative means for programming controller 28,30, in addition to the keypad and touch screen mentioned above.

In another approach for programming controllers 28,30, controller 30 may define an input slot 54 which is sized to receive an input device, such as a flash memory card 56 or other removable memory device, which carries input data for controllers 28,30. This removable memory device may be programmed by the controller 30 or some external device, such as a remote computer. For example, the removable memory may be inserted into and programmed by a computer at a physician's office, hospital, clinic, or other health facility and given to the subject for use with the applicator. Indeed, use of the flash memory card 56 or similar memory device in conjunction with controller 30, may result in the only other input device of controller 30 being switch 34. Thus, programmable removable memory provides yet another alternative means for programming the applicator controller, in addition to the keypad, touch screen, and remote computer connection described above.

In one specific embodiment, controller 30 may only have an ON switch 42, and be completely preprogrammed via an external computer 52, such as at a doctor's office or pharmacy, prior to giving the device to a patient. In another embodiment, the device may be sold with only an ON switch 42, and with the physician or pharmacy supplying the medication in a kit with a flash memory card 56.

FIG. 3 illustrates another embodiment of a dispensing apparatus, indicated generally at 100, for administering a fluid to one or both eyes of a user 8. This embodiment shares many similarities with the embodiment of FIGS. 1 and 2. Hence, components in FIG. 3 that are identical to corresponding components in FIGS. 1 and 2 have the same respective reference numerals and are not described further.

One difference between apparatus 10 of FIGS. 1 and 2 and apparatus 100 of FIG. 3 is that the latter includes fluid dispensers 102 and 104 that generally conform to the shape of rims 26a, 26b of the frame 12. Nozzles or orifices 110 for ejecting droplets of fluid are formed along the length of the dispensers 102, 104. Apparatus 100 also includes digital cameras 106 supported by arms 108 extending from the front of the eye piece 22 of the frame 12. Each camera 106 is positioned to capture digital images of an adjacent eye. Images captured by cameras 106 can be displayed on the display screen 46 of controller 30 or the monitor of computing device 52 for the purpose of, for example, monitoring the general condition of an eye or the condition of an eye in response to a medication. Eye images can be saved in a historical data file, which then can be used by a physician at a later time to monitor the condition of a subject. Cameras 106 also can be used to capture digital images of the eyes as part of an eye-positioning system, as described below.

Figure 4:
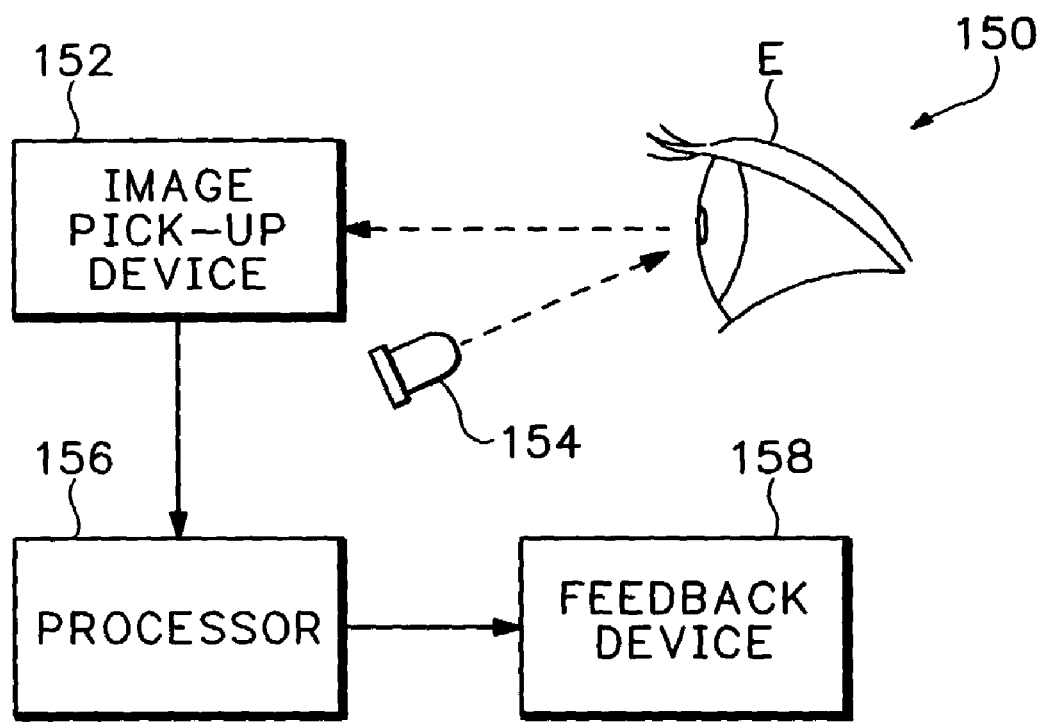
FIG. 4 is a block diagram of an eye-positioning device for assisting a user in moving an eye to a predetermined position for administering a fluid to the eye.

In some applications, to effectively administer a fluid, it may be necessary to apply the fluid to a specific location on the ocular surface, such as the corner or lower portion of the eye. To such ends, an eye-positioning system can be implemented to facilitate proper positioning of one or both eyes for administering the fluid. FIG. 4 illustrates one embodiment of an eye-positioning system, indicated generally at 150. The illustrated eye-positioning system 150 includes an image pick-up device 152 positioned in front of an eye E of a user and configured to capture an image of the eye E. A light source 154, such as a light emitting diode (LED), can be used to illuminate the anterior part of the eye E. An analog-to-digital converter (ADC) (not shown), which can be separate from or part of the image pick-up device 152, produces a digitized signal of the image.

The digitized signal is inputted into a processor 156 to determine whether the eye is the proper position for administering a fluid to a selected location on the surface of the eye. In this manner, the image pick-up device 152 and the processor 156 serve as an eye-position detector for detecting the position of the eye. The processor 156 can be a general purpose computing device or a specialized device having processing capabilities. A feedback device 158 (also referred to herein as a feedback mechanism) receives a signal from the processor 156 corresponding to the current position of the eye. Based on this signal, the feedback device 158 outputs feedback information that assists the user in moving the eye to a position relative to a fluid dispenser that will enable the fluid dispenser to dispense the fluid onto the selected location on the eye surface. When the processor 156 detects that the eye is in the desired position, the feedback device instructs the user to hold the eye in its current position for administering the fluid.

The image pick-up device 152 can be a digital camera (either a still camera or a video camera) that uses conventional imaging technology, such as a charged coupled device (known as a CCD sensor), a complementary metal oxide semiconductor (known as a CMOS sensor), or other types of image sensors. Other types of optical systems and methods can also be implemented for capturing an image of the eye, such as disclosed in U.S. Pat. No. 6,494,577 to Iwanaga (the '577 patent) or U.S. Pat. No. 6,520,640 to Binnun, which are incorporated herein by reference.

The feedback information generated by feedback device 158 can be any of various audible, visual, or tactile cues or signals. In one implementation, the feedback device generates vocalizations instructing the patient to move the eye to a specific position for administering a fluid. The vocalizations can be, for example, simple instructions, such as "up," "down," "left," "right," and "hold" to indicate that the eye is in the proper position for administering the fluid.

In another implementation, the feedback device 158 emits a continuous tone that changes in volume or pitch to indicate the direction in which the eye is to be moved, and then emits a pulsing tone or other distinctive sound when the eye is in the desired position. The change in volume or pitch can be a gradual change, increasing as the eye moves toward the desired position and decreasing as the eye moves away from the desired position.

In another implementation, the feedback device 158 provides visual cues, such as by illuminating lights or displaying text or symbols on a display screen (e.g., display screen 46) that assist the user in moving the eye to the desired position.

The feedback device 158 also can provide tactile signals, such as vibratory or vibrating signals similar to those used on pager devices and wireless phones.

The eye-positioning system shown generally in FIG. 4 can be implemented in the dispensing apparatus 100 of FIG. 3. In this embodiment, cameras 106 serve as image pick-up devices for capturing images of the eyes. Dispensing apparatus 100 can be operatively connected to either controller 30 or computer 52, such as shown in FIG. 1. Either controller 30 or computer 52 can be programmed to perform the processing functions of processor 156 described above. Controller 30 can be configured to serve as the feedback device 158. In particular embodiments, for example, controller 30 includes hardware for generating audible feedback signals, such as discussed above. In addition, visual feedback signals (e.g., text, symbols, or combinations thereof) can be displayed on the display screen 46 of the controller 30. In other embodiments, the feedback device and controller 30 are separate devices.

Figure 5:
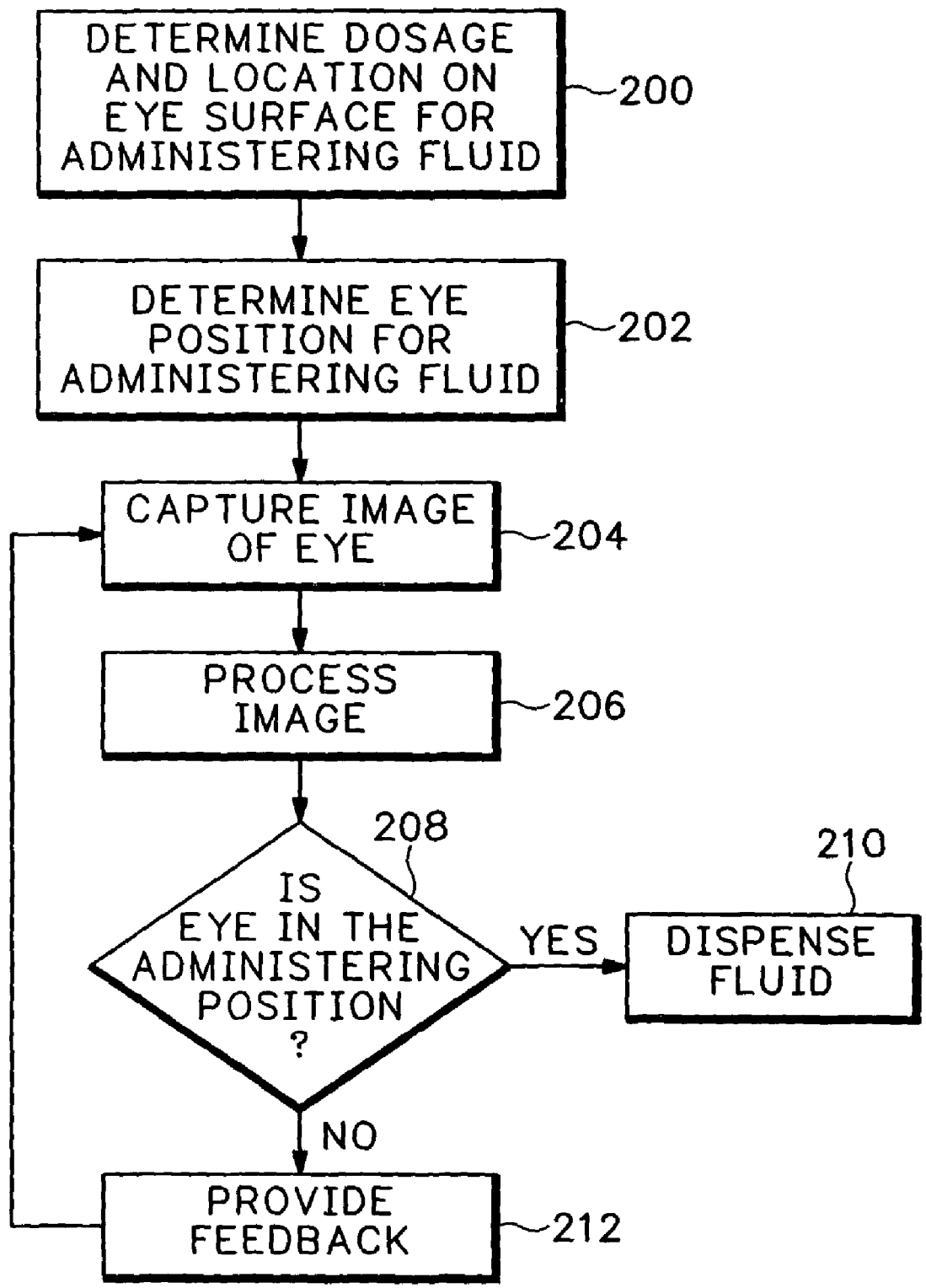
FIG. 5 is a flowchart illustrating one embodiment of a process for operating an ophthalmic apparatus for administering a fluid to an eye.

FIG. 5 is a flowchart illustrating one embodiment of a process for operating an ophthalmic apparatus having the eye-positioning system 150. As indicated at 200, a user or health care professional selects the dosage of the fluid to be applied to an eye and the location on the eye that is to receive the fluid. This information is inputted into the processor 156, such as via a user-interface software program, as further described below, or other input devices. The selected location on the eye can be a specific location or a general area on the surface of the eye. The processor 156 then determines an administering position for the eye (as indicated at 202); that is, the position for the eye relative to a fluid dispenser (e.g., dispenser 102 or 104) that will allow fluid to be dispensed onto the selected location of the eye.

Once the administering position for the eye is determined, the image pick-up device 152 captures an image of the eye (as indicated at 204) and a digitized image of the eye is generated by the ADC. As indicated at 206, the processor 156 receives the digitized image from the image pick-up device 152 and generally (1) processes the image to determine the position of a reference location on the eye (e.g., the pupil), (2) detects the current position of the eye by determining the offset of the reference location on the eye from a fixed reference point (e.g., a fixed point on an adjacent fluid dispenser), and (3) determines whether the eye is in the administering position (as indicated at 208).

The processor 156 then outputs a signal to the feedback device 158 corresponding to current position of the eye. For example, if the processor 156 detects that the eye is in the administering position, the processor 156 signals the feedback device 158 to instruct the user to hold the current eye position and the fluid is automatically administered to the selected location of the eye surface (as indicated at 210). On the other hand, if the processor 156 detects that the eye is not in the administering position, the processor 156 signals the feedback device to generate an appropriate feedback signal (as indicated at 212) to the user.

In particular embodiments, the processor 156 detects the position of the center of the pupil to determine the position of the eye relative to a fixed reference point. There are several processing techniques that can be used to detect the position of the center of the pupil. In one method, for example, the eye is illuminated so that the anterior eye image becomes darkest in the pupil and brighter in the iris. The processor 156 then detects the center of the pupil based on the contrast between the pupil and the region surrounding the pupil, as known in the art and as discussed in the '577 patent to Iwanaga and U.S. Pat. No. 6,280,436 to Freeman et al.

As shown in FIG. 5, after the feedback device 158 outputs a feedback signal (212), the steps of capturing an image of the eye (204), processing the image (206), and determining whether the eye is in the administering position (208) are repeated until the processor 156 detects that the eye is in the administering position. To ensure that the user has enough time to react to a feedback signal before the next feedback signal is generated, a suitable delay period (e.g., one second or more) can be implemented between the steps of providing a feedback signal (212) and capturing another image of the eye (204). In an alternative approach, the camera continuously outputs a succession of images of the eye and the processor 156 is programmed to periodically (e.g., every two seconds) select an image for further processing.

In an alternative embodiment, the image pick-up device 152 continuously outputs a succession of images of the eye to the processor 156. The processor 156 processes each image and the feedback device 158 provides a new feedback signal only if the processor detects movement of the reference location of the eye or if the reference location on the eye has moved from a predetermined distance from a previous image. In another embodiment, the feedback device 158 provides an initial feedback signal and generates additional feedback signals only if the processor 156 detects movement of the eye in the wrong direction (i.e., the user is moving the eye away from the administering position).

In addition to the feedback device embodiments described above, an eye-positioning system can provide feedback in the form of a visual target to assist a patient to position the eye in a desired position relative to a fluid dispenser for administering a fluid. In one embodiment, for example, an eye-positioning system includes a miniature display, such as used in digital cameras, that displays a real-time image of the eye along with a target (e.g., across-hair pattern). The display is mounted in any convenient position that allows the patient to view the images on the display. The target is positioned on the display such that when the patient aligns a reference location of the eye (e.g., the pupil), the eye is in the desired position for administering the fluid. In this manner, the target serves as a cue or signal to assist the patient in positioning the eye. In some embodiments, the display is operable to illuminate the target when the reference location of the eye is aligned over the target to indicate that the eye is correctly positioned.

In one specific embodiment, apparatus 100 of FIG. 3 is modified to include a miniature video display mounted to one or both sides of the frame 12. For example, each display can be mounted to a respective extension bracket extending in front of eye-piece 22 in a manner similar to cameras 106. Each display is operatively connected to a respective camera 106 and therefore is operable to display a real-time image of the respective eye. Each display displays a target that allows the patient to self-align a reference location on the eye.

In another embodiment, an eye-positioning system includes an image pick-up device (e.g., image pick-up device 152), a light source (e.g., LED 154), and a processor (e.g., processor 156). In this embodiment, the subject moves the eye generally toward the administering position, or alternatively, the user moves the eye randomly or in a particular manner (e.g., side-to-side, up and down, or in a circular pattern). The image pick-up device continuously outputs images of the eye to the processor, which continuously tracks the position of the selected location on the eye that is to receive fluid from a fluid dispenser. When the eye is in the administering position, the fluid is automatically dispensed onto the surface of the eye. In this embodiment, a feedback device may be used to alert or inform the subject to stop moving the eye and hold the current position when the eye is in the administering position.

Figure 6:
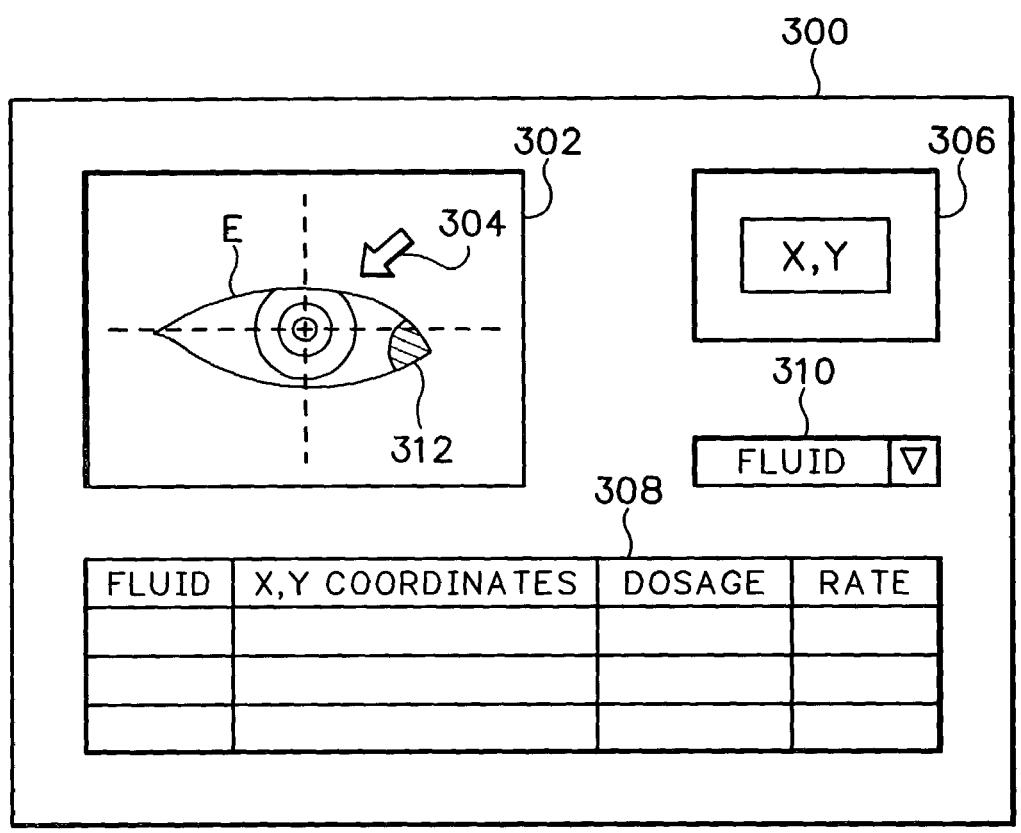
FIG. 6 is an embodiment of a user interface software program for setting the operating parameters of the ophthalmic apparatus, such as the apparatus of FIG. 1 or FIG. 3.

FIG. 6 illustrates an embodiment of a user-interface software program for use with an ophthalmic apparatus, such as the embodiment shown in FIG. 1 or FIG. 3. The program can be used for setting various operating parameters of an ophthalmic apparatus, monitoring the condition of a patient's eye, or saving images and other data that is useful in treating a patient. The program can be implemented in various programming languages and operating systems. In one implementation, for example, the program is configured to run on a computer having the WINDOWS operating system of Microsoft Corporation of Redmond, Wash.

The software program described herein is stored on a computer-readable medium and executed on a general-purpose computer (e.g., computer 52 shown in FIG. 1). It should be understood, however, that the invention is not limited to any specific computer language, program, operating system or computer. In addition, those of ordinary skill in the art will recognize that devices of a less general-purpose nature, such as hardwire devices, or the like, may also be used.

According to one embodiment, a system implementing the software program includes the computing device 52 (FIG. 1) for executing the program and acquiring user input, controller 30 (FIG. 1), and dispensing apparatus 100 (FIG. 3). In this embodiment, an eye-positioning system includes cameras 106 and controller 30, which has processing and feedback capabilities. By way of example, the following description of the software program proceeds with reference to the foregoing embodiment. However, the program also can be implemented in various other systems.

The program desirably includes a plurality of graphical user interface elements that allow a user or health care professional to set or select certain operating parameters of the dispensing apparatus 100. Without limitation, graphical user interface elements can be buttons, checkboxes, drop-down pick lists, edit boxes, pop-up menus, a movable cursor or pointer, and the like, as generally known in the art. FIG. 6 illustrates an exemplary embodiment for implementing various user interface elements for controlling the operation of a dispensing apparatus. The types and/or number of interface elements used can be varied in alternative implementations.

As shown in FIG. 6, the program includes a main display screen or window 300. The illustrated display screen 300 includes an image display area 302 that displays an image of an eye E captured by a camera 106. If both eyes of the patient are being treated, the display screen 300 can include another display area 302 to display an image of the other eye. In any event, the eye image displayed in area 302 can be an image immediately downloaded from the camera 106 or an image previously captured and saved in a data file.

The display area 302 also displays a coordinate system having its origin at a reference location on the eye surface (in this case, the center of the pupil) so that any location on the eye surface can be identified by its x,y coordinates. Using a pointing device (e.g., a mouse), a user can move a cursor 304 within the display area 302 and select a specific location on the eye surface that is to be sprayed by a respective fluid dispenser 102, 104 of the dispensing apparatus 100. An x,y readout 306 continuously displays the x,y coordinates of the cursor 304 as the cursor 304 is moved within the display area.

Depending on the application, the selected location can be a discrete point on the eye surface or a selected area on the eye surface. For example, if a certain treatment calls for applying a bioactive composition generally to the corner of the eye E, the patient or health care professional, using the pointing device, can define an area 312 at the corner of the eye. The position of a selected area, such as area 312, relative to the origin can be defined by the x,y coordinates of the center of the selected area. After the x,y coordinates of the selected location are identified, the program determines an administering position for the eye that will allow the respective fluid dispenser 102, 104 to dispense the fluid onto the selected location of the eye surface.

A data table 308 displays data for various operating parameters of apparatus 100, including the x,y coordinates of the selected location, dosage, dispensing rate, and fluid. As shown, the data table 308 contains multiple rows of data, each corresponding to a particular treatment protocol. In one implementation, each data cell in data table 308 is an edit box that allows the user to enter the required data into the data table 308. Alternatively, this data can be imported from a data file. Other techniques can be implemented to acquire values for the operating parameters. In the illustrated embodiment, for example, the display screen 300 includes a drop-down pick list 310 for selecting the particular fluid to be administered.

In addition to the operating parameters shown in the data table 308, the program can be used set various other operating parameters, such as those described above in connection with controllers 28 and 30. In any event, once defined, the operating parameters can be downloaded to the controller 30.

The specification has described several detailed examples, which are not intended to be limiting. Rather, these examples are provided to illustrate some of the embodiments which come within the scope of the following claims.

We claim:

1. An ophthalmic apparatus comprising:
an eye-positioning device comprising:
an image pick-up device configured to capture a digital image of the eye;
an image processor configured to process the digital image of the eye and determines whether the eye is in a desired position;
an electronic feedback device configured to provide information to a subject who is moving an eye from a current position to the desired position relative to the eye positioning device; and
an applicator configured to dispense a fluid into the eye conditionally upon positioning of the eye in the desired position.

2. The apparatus of claim 1, wherein the electronic feedback device is operable to provide audible cues that assist the subject in moving the eye to the desired position.

3. The apparatus of claim 1, wherein the electronic feedback device is operable to provide visual cues that assist the subject in moving the eye to the desired position.

4. The apparatus of claim 1, wherein the eye-positioning device comprises a display for displaying a real-time image of the eye and a target, such that when the eye is aligned with the target, the eye is in the desired position.

5. The apparatus of claim 1, wherein the image pick-up device comprises a CCD camera.

6. The apparatus of claim 1, wherein the information provided to the subject by the electronic feedback device comprises feedback signals, the feedback signals corresponding to directions for moving the eye to the desired position.

7. The apparatus of claim 1, wherein the applicator comprises:
a frame for wearing on the head of the subject; and
a fluid dispenser supported by the frame proximate the eye of the subject, the fluid dispenser configured to dispense fluid into the eye.

8. The apparatus of claim 7, wherein the frame comprises a spectacle frame.

9. The apparatus of claim 7, wherein the fluid dispenser comprises a jet dispenser.

10. The apparatus of claim 9, wherein the fluid dispenser comprises a piezoelectric jet dispenser.

11. The apparatus of claim 9, wherein the fluid dispenser comprises a thermal droplet jet dispenser.

12. The apparatus of claim 7, wherein the applicator further comprises a controller operable to actuate the fluid dispenser.

13. The apparatus of claim 12, wherein the controller is operable to control the fluid dispenser to dispense a predetermined dosage of fluid into the eye.

14. The apparatus of claim 7, wherein the applicator further comprises a fluid reservoir for storing the fluid and delivering the fluid to the fluid dispenser.

15. The apparatus of claim 1, wherein the applicator comprises:
   a jet dispenser having a plurality of ejection orifices; and
   a controller operable to control the jet dispenser to dispense fluid from one or more selected ejection orifices.

16. The apparatus of claim 1, further comprising a user interface program for acquiring user input for setting one or more operating parameters of the apparatus.

17. The apparatus of claim 16, wherein the user interface program comprises a graphical user interface element for setting one or more operating parameters of the apparatus.

18. An ophthalmic apparatus, comprising:
   a dispensing apparatus configured to dispense fluid into an eye of a subject;
   an eye-position detector configure to detect a current position of the eye relative to the dispensing apparatus; the eye-position detector comprising:
      an image-capturing device configured to capture and outputs a digitized image of the eye; and
      a processor configured to receive the digitized image, processes the digitized image, and determines the current position of the eye relative to a predetermined position from the digitized image; and
   a feedback device configured to receive information from the eye-position detector corresponding to the position of the eye,
      wherein the feedback device provides feedback information to the subject that assists the subject in moving the eye from the current position to a predetermined position relative to the dispensing apparatus for administering the fluid to the eye.

19. The apparatus of claim 18, wherein the dispensing apparatus comprises a spectacle frame for wearing on the head of the subject and a fluid dispenser carried by the frame and configured to propel fluid into the eye.

20. The apparatus of claim 18,
   in which the processor is configured to output an output signal to the feedback device corresponding to the current position of the eye relative to the predetermined position; and
   the feedback device is configured to receive the signal from the processor and output a feedback signal that assists the subject in moving the eye to the predetermined position relative to the dispensing apparatus.

21. The apparatus of claim 19, wherein the image-capturing device comprises
   a digital camera configured to generate the digitized image at the eye, the camera being supported by the frame.

22. The apparatus of claim 18, wherein the processor comprises a controller, the controller being operable to control the fluid dispenser to dispense the fluid.

23. The apparatus of claim 22, wherein the controller controls the fluid dispenser to dispense the fluid when the processor detects that the eye is in the predetermined position.

24. An ophthalmic apparatus for administering a liquid to an eye of a subject, comprising:
   means for detecting the position of the eye;
   means for receiving information corresponding to a current position of the eye from the means for detecting the position of the eye,
      wherein the means for receiving information corresponding to the current position of the eye provides feedback information to the subject that assists the subject in moving the eye from the current position to a predetermined position relative to the ophthalmic apparatus; and
   means for dispensing the liquid into the eye only when the eye is in the predetermined position.

25. The apparatus of claim 24, wherein the means for detecting the position of the eye comprises:
   means for capturing an image of the eye; and
   means for determining the position of the eye relative to the predetermined position based on the image of the eye.

26. The apparatus of claim 24, wherein the ophthalmic apparatus further comprises means for providing an audible or visual feedback signal to the subject to assist the subject in moving the eye to the predetermined position.

27. A method for administering a liquid to an eye of a subject, comprising:
   with an image pick-up device, capturing a digital image of the eye;
   detecting the position of the eye relative to a predetermined position with an eye position detector;
   automatically providing feedback information to the subject if the eye-position detector detects that the eye is not in the predetermined position so that the subject can move the eye to the predetermined position; and
   dispensing the liquid into the eye with a liquid dispenser if the eye is in the predetermined position.

28. The method of claim 27, wherein dispensing the liquid into the eye comprises dispensing the liquid from a jet dispenser.

29. The method of claim 28, wherein the jet dispenser comprises a plurality of ejection nozzles and dispensing the liquid comprises dispensing the liquid from one or more selected nozzles of the plurality of nozzles.

30. The method of claim 27, further comprising processing the digital image to determine the position of the eye relative to the predetermined position.

31. The method of claim 27, further comprising selecting a location on the eye surface for administering the liquid, prior to detecting the position of the eye.

32. The method of claim 27, further comprising acquiring from user input, via a user interface software program, one or more operating parameters of the liquid dispenser.

33. The method of claim 27, wherein one of said operating parameters is the dosage of the liquid to be dispensed into the eye.

34. A system for administering a fluid to an eye of a subject, comprising:

an image pick-up device configured to capture an image of the eye and generate a digitized image of the eye;

an image process configured to process the digital image of the eye to determine whether the eye is in a predetermined position for administering the fluid to the eye;

an electronic feedback device configured to generate a feedback signal to the subject if the image processor determines that the subject's eye is not in the predetermined position, the feedback signal comprising an audible or visual signal corresponding to a direction for moving the eye toward the predetermined position;

an applicator configured to dispense the fluid into the eye when the eye is in the predetermined position, the applicator comprising a spectacle frame for wearing on the head of the subject, a fluid reservoir for containing the fluid, and a jet dispenser supported by the frame proximate the eye, the jet dispenser being fluidly connect to the fluid reservoir for receiving the fluid, the jet dispenser configured to dispense a controlled amount of the fluid into the eye;

a controller configured control the jet dispenser to dispense the fluid; and a user interface software program configured to acquire user input for setting operating parameters of the system.

* * * * *

UNITED STATES PATENT AND TRADEMARK OFFICE
CERTIFICATE OF CORRECTION

PATENT NO. : 8,128,606 B2
APPLICATION NO. : 10/613842
DATED : March 6, 2012
INVENTOR(S) : Daryl E. Anderson et al.

Page 1 of 1

It is certified that error appears in the above-identified patent and that said Letters Patent is hereby corrected as shown below:

In column 17, line 6, in Claim 34, before "configured" delete "process" and insert -- processor --, therefor.

In column 18, line 10, in Claim 34, after "configured" insert -- to --.

Signed and Sealed this
Eleventh Day of December, 2012

David J. Kappos
*Director of the United States Patent and Trademark Office*